United States Patent
Ersue et al.

(10) Patent No.: US 7,639,349 B2
(45) Date of Patent: Dec. 29, 2009

(54) METHOD AND SYSTEM FOR INSPECTING SURFACES

(75) Inventors: Enis Ersue, Darmstadt (DE); Joerg Amelung, Darmstadt (DE)

(73) Assignee: Isra Vision System AG, Darmstadt (DE)

( * ) Notice: Subject to any disclaimer, the term of this patent is extended or adjusted under 35 U.S.C. 154(b) by 380 days.

(21) Appl. No.: 10/587,641

(22) PCT Filed: Feb. 10, 2005

(86) PCT No.: PCT/EP2005/001310

§ 371 (c)(1),
(2), (4) Date: Jul. 28, 2006

(87) PCT Pub. No.: WO2005/090950

PCT Pub. Date: Sep. 29, 2005

(65) Prior Publication Data

US 2007/0153261 A1    Jul. 5, 2007

(30) Foreign Application Priority Data

Feb. 18, 2004    (DE)    ........................ 10 2004 007 828

(51) Int. Cl.
*G01N 21/00* (2006.01)
(52) U.S. Cl. .................................. 356/237.1; 356/237.2
(58) Field of Classification Search ........................ None
See application file for complete search history.

(56) References Cited

U.S. PATENT DOCUMENTS

| 2,315,282 | A | * | 3/1943 | Snow | .......................... 356/446 |
| 4,918,321 | A | | 4/1990 | Klenk et al. | |
| 5,142,648 | A | | 8/1992 | Fitts et al. | |
| 5,438,525 | A | | 8/1995 | Shimbara | |

FOREIGN PATENT DOCUMENTS

| DE | 37 12 513 | 11/1988 |
| DE | 43 38 223 | 5/1994 |
| DE | 197 39 250 | 3/1998 |
| WO | 87/00629 | 1/1987 |

* cited by examiner

*Primary Examiner*—Gregory J Toatley, Jr.
*Assistant Examiner*—Amanda H Merlino
(74) *Attorney, Agent, or Firm*—Michael J. Striker

(57) ABSTRACT

The method of inspecting the surface of a three-dimensional body, includes moving at least one camera and at least one illuminating device relative to the surface of the three-dimensional body, taking pictures of the areas of the surface to be inspected during the movement of the at least one camera relative to the areas of the surface to be inspected, transmitting the pictures taken to a computer and evaluating the pictures in the computer to find any defects that are present. A system for performing the method is also described. In order to obtain high inspection quality, the camera, illumination device and the surface to be inspected are brought into plural different defined geometric relationships with each other during the inspecting of each of the areas on the surface, at least for a time period required to take one picture.

18 Claims, 2 Drawing Sheets

METHOD AND SYSTEM FOR INSPECTING SURFACES

CROSS-REFERENCE

This is the U.S. National Stage of PCT/EP 2005/001310, which was filed on Feb. 10, 2005, in Europe. The invention described and claimed herein below is also described in German Patent Application 10 2004 007 828.9, which was filed on Feb. 18, 2004 in Germany. The aforesaid German Patent Application provides the basis for a claim of priority of invention for the invention claimed herein below under 35 U.S.C. 119 (a)-(d).

BACKGROUND OF THE INVENTION

The present invention relates to a method for inspecting the surfaces of a three-dimensional body, with which at least one camera and at least one illuminating device are moved relative to the surface of the object, pictures are taken of the areas to be inspected on the surface during the movement of the camera relative to the surface, and the pictures are transmitted to a computer and evaluated therein. The invention also relates to a corresponding system for inspecting surfaces.

The three-dimensional object can be a body or a body part, in particular. In this case, the surface to be inspected is often a painted surface or a bare sheet-metal surface, the quality of which is to be inspected. The inspection is carried out to identify defects or flaws, such as topological defects, on the surface using optical scanning. The camera used for this purpose can be any optical picture-taking device that meets the particular requirements and is optimally adapted to the surface to be investigated.

A similar inspection system is known, e.g., from U.S. Pat. No. 5,142,648, with which a large number of illumination units and cameras is installed along a production line for passenger vehicles, the signals of which are evaluated in an arithmetic logic unit. This system has the problem, however, that the entire three-dimensional object cannot be examined with equal inspection quality in all areas to be inspected on the surface, because the picture-taking conditions are too different for the various areas.

SUMMARY OF THE INVENTION

The object of the present invention, therefore, is to provide a possibility for inspecting surfaces, with which all areas to be inspected on the surface can be examined with the same level of quality.

This object is essentially attained by a method of the type described initially, in which the camera, the illumination device and the surface are brought into a defined geometric relationship with each other during the inspection of each area to be inspected on the surface, at least for the period of time required to take a picture. In this manner, at least one picture of each of the areas to be inspected is obtained that is equal to the rest of the pictures of the other areas to be inspected in terms of the picture-taking situation and quality. A high level of inspection quality is ensured as a result. The geometric relationship to be attained can be specified for every inspection in accordance with the particular requirements. A control computer ensures that an inspection unit with a camera and illumination device and, e.g., the surface to be inspected on the body, are moved relative to each other in a suitable manner. It is particularly advantageous when one or more inspection units and the object itself to be inspected are controlled in a coordinated manner, e.g., using a single control computer. It is then possible to perform other types of work on the object during the inspection and while the object is moving. This is particularly space-saving and is therefore particularly well-suited for use on complicated production or processing lines, with which the greatest possible number of tasks must be performed along the shortest possible path. The picture-taking position can be defined, in particular, by an angle at which the picture-taking is carried out, and/or via the resolution of the picture-taking. The resolution can be controlled via the distance at which the picture is taken, via the selection of the focal distance of camera lenses, or the like.

The relative motion between the camera, the illumination and surface to be inspected can be produced by moving the object that is the three-dimensional body independently of the optical systems defined by the camera and the illumination device, by measuring this motion, and by optionally adapting a motion of the optical system to the independent motion of the object. This variation is advantageous particularly when the inspection system according to the present invention must be adapted to an existing production line. It is possible to also design cameras and illumination devices—which can be combined into a single inspection unit—to be stationary, in which case several different inspection units or cameras and illumination devices are then preferably provided at various positions. Furthermore, the relative motion can also be brought about by ensuring that the object to be inspected is stationary and then moving the camera with the illumination device over the three-dimensional object. A combination of the possibilities described above is also feasible. The relative motion can be specified particularly easily when all displacement devices are synchronized with each other. This makes it possible to also easily inspect the moving object, since the relative motion of camera/illumination and the object is coordinated.

It can be advantageous to combine at least one camera and at least one illumination device into one inspection unit and to move them together. The same illumination situation is attained for each camera orientation by specifying a relatively fixedly specified orientation between the camera and the illumination device. The inspection unit is then moved in a manner that is controlled as a function of the object motion that is measured. An inspection unit can then include several cameras and/or light sources.

According to a preferred embodiment, the camera, illumination device and the surface are brought into a defined geometric relationship with each other during the inspection of each area to be inspected on the surface, at least for the period of time required to take a picture. Since certain surface defects can be found only in a certain picture-taking position, which can differ from the picture-taking position for another defect type, different defects can also be reliably detected in this manner.

According to the present invention, the defined geometric relationship can be determined by the angle between the surface of the area to be inspected, the illumination and the camera and/or by the distance between the surface of the area to be inspected and the illumination and/or the camera. Based on the known positions of the three-dimensional body, the illumination and the camera, the control computer can identify these relationships for every area to be inspected and thereby ensure—for each area to be inspected—that the defined geometric relationship was attained at least once during the entire inspection.

According to the inventive method, it is also possible to select different-sized areas to be inspected, depending on the curvature of the surface. This is advantageous, in particular, when the curvature is designed such that defects can no longer be detected unambiguously, due to the curvature. In most practical cases, however, the entire image can be evaluated.

To allow easy adjustment of the geometric relationship for every area to be inspected, it is provided according to the present invention that the camera, the illumination device and/or body with the surface to be inspected are movable in one or more degrees of freedom. Preferably, at least one displacement device is provided for this purpose, on which the camera, illumination device and/or body are mounted. Possible displacement devices include, e.g., a manipulator, a handling device, or a multiaxial traveling unit with linear traveling axes and/or axes of rotation.

Depending on the structure of the surface to be inspected, the illumination can take place in a diffuse, directed or structured manner, as sustained picture-taking and/or a flash picture-taking. The illumination can be alternating dark-field and/or bright-field illumination and/or a—preferably directed—two-dimensional illumination. It is also possible to project suitable patterns.

In order to also enable identification of various surface defects, it can be advantageous according to the present invention to take several pictures of an area to be inspected on the surface under various illumination situations and/or with different camera settings. The camera setting can include the orientation of the camera, and the picture-taking parameters, such as aperture, shutter speed, or the like. These parameters can be adapted, preferably automatically, to various surface properties, such as color and reflectivity. The same applies for the type of illumination. The surface properties are recognized via the image evaluation. The parameter adaptation is carried out preferably automatically and in a self-learning manner.

According to a particularly preferred embodiment of the inventive method, several cameras and several illumination devices are combined to form at least two subsystems that are movable relative to the surface to be inspected, the subsystems being interconnected via a communication interface, and the inspection result being obtained by evaluating the images of several or all of the subsystems. A subsystem is composed of at least one camera and one illumination device. The subdivision into several subsystems allows a three-dimensional body to be inspected more quickly overall, since pictures can be taken of various areas simultaneously, and/or various geometric relationships can be attained simultaneously for an area to be inspected.

An advantageous application is, e.g., the simultaneous monitoring of large and small surface areas. To this end, the subsystems composed of camera and illumination device are each adapted to the special monitoring task. For small areas, the system can include, e.g., an illumination device and a camera. For a large area, several adjacent cameras and illumination systems can be combined into one subsystem, so that a particularly large area to be inspected can be covered all at once using this subsystem. Some of the subsystems can have a displacement device for moving the subsystems, or they can be located such that they are stationary next to the moving object. The type of camera and the illumination can also differ from subsystem to subsystem.

According to the inventive method, after the pictures are taken, they are evaluated, preferably with the aid of image-evaluation algorithms stored in a computer system. This image evaluation is generally known. It can be provided, according to the present invention, however, to except specifiable structures from detection as defects during the inspection. During painting, defects can occur, which are caused, e.g., by dirt particles located on the surface during painting or due to wetting problems on the surface. In accordance with the structures recognized in the inspection, the defects are then classified accordingly; this makes it possible to except certain defects from being recognized as defects during the inspection, or to specify various classes of defects. In the image evaluation, it is possible to evaluate the size, contrast, relationship between size and contrast, the geometry and contour, such as the identification of a surrounding edge of a certain contrast area, and/or the positioning of the defect in the bright field or dark field, when bright-field/dark-field illumination is carried out. The image-evaluation algorithms can be adapted to various surface properties, e.g., via the suitable selection of algorithms or parameterization.

With the inventive method, the relative position between the surface to be inspected and the camera and/or the illumination device is detected, and the picture is taken such that it is controlled via resolution, position and/or time, in particular, as a function of the relative position. By way of this control, which is specified, e.g., using a control computer, it can be ensured in a particularly simple manner that a picture of every area to be inspected is taken at the right time, i.e., when the relative position between body, camera and illumination conforms with the specified relationship.

According to an advantageous embodiment of the present invention, the relative position between the camera and the object and/or the illumination device can be detected by taking a picture using sensors. This picture is analyzed by the image-evaluation system. Based on this, the particular coordinates and positions are determined in an absolute and/or relative manner. Based on these automatically determined positions, the camera, object and/or illumination device can then be oriented automatically. For object recognition, geometric features or the appearance of the surface, for example, can be specified as orientation features to the image-evaluation system. In addition or as an alternative thereto, the positions can also be detected using other sensors.

Finally, it is possible to inspect different specified areas to be inspected on the surface using different settings in the geometric relationship, the illumination situation and/or in image-processing parameters, when the purpose is to detect various defects, e.g., in the different areas. Different quality ranges can be established in this manner, for example.

The object according to the present invention is also attained by a system for inspecting surfaces of a three-dimensional body, which can be used, in particular, to carry out the method described above. The system has a camera for taking pictures of the areas to be inspected on the surface, and at least one illumination device, at least one displacement device that moves the camera, illumination device and body relative to one another, and an evaluation unit for evaluating the pictures that were taken. A control device of the system is set up, according to the present invention, such that the camera, illumination device and the surface are in and/or are brought into at least one defined geometric relationship with each other during the inspection of each area to be inspected on the surface, at least for the period of time required to take a picture. As a result, a consistent level of picture-taking quality can be attained for every area to be inspected, and a high defect detection rate can be attained.

Preferably, at least one camera and at least one illumination device are located in a single inspection unit, so that the geometric relationship between the camera and the illumination device in this inspection unit is always specified in a fixed manner. Particularly advantageously, several cameras can also be provided per inspection unit, the optical axes of which are possibly oriented differently, so that pictures of an area to be inspected can be taken simultaneously from different perspectives.

Furthermore, according to the present invention, several cameras and illumination devices or inspection devices can each represent separate subsystems, each of which is connected with the evaluation device and the control device. By inspecting various surface areas simultaneously, the inspection time can be reduced considerably. The subsystems can also be suitable, in particular, for different-sized inspection areas.

In a particular embodiment of the inventive system, at least one stationary and one movable subsystem are provided.

To identify the specified geometric relationship, it is particularly advantageous when the cameras used are calibrated three-dimensionally, so that the relative orientation between camera and object can also be determined from the camera image and a known position of a known object. The camera is then preferably calibrated with reference to illumination devices, the object and displacement devices, so that the relative positions are known exactly at any time.

BRIEF DESCRIPTION OF THE DRAWING

The present invention is explained below in greater detail with reference to an exemplary embodiment and the drawing. All of the features described and/or depicted graphically are part of the present invention, independently of their wording in the claims or their back-references.

DETAILED DESCRIPTION OF THE INVENTION

Figure 1:
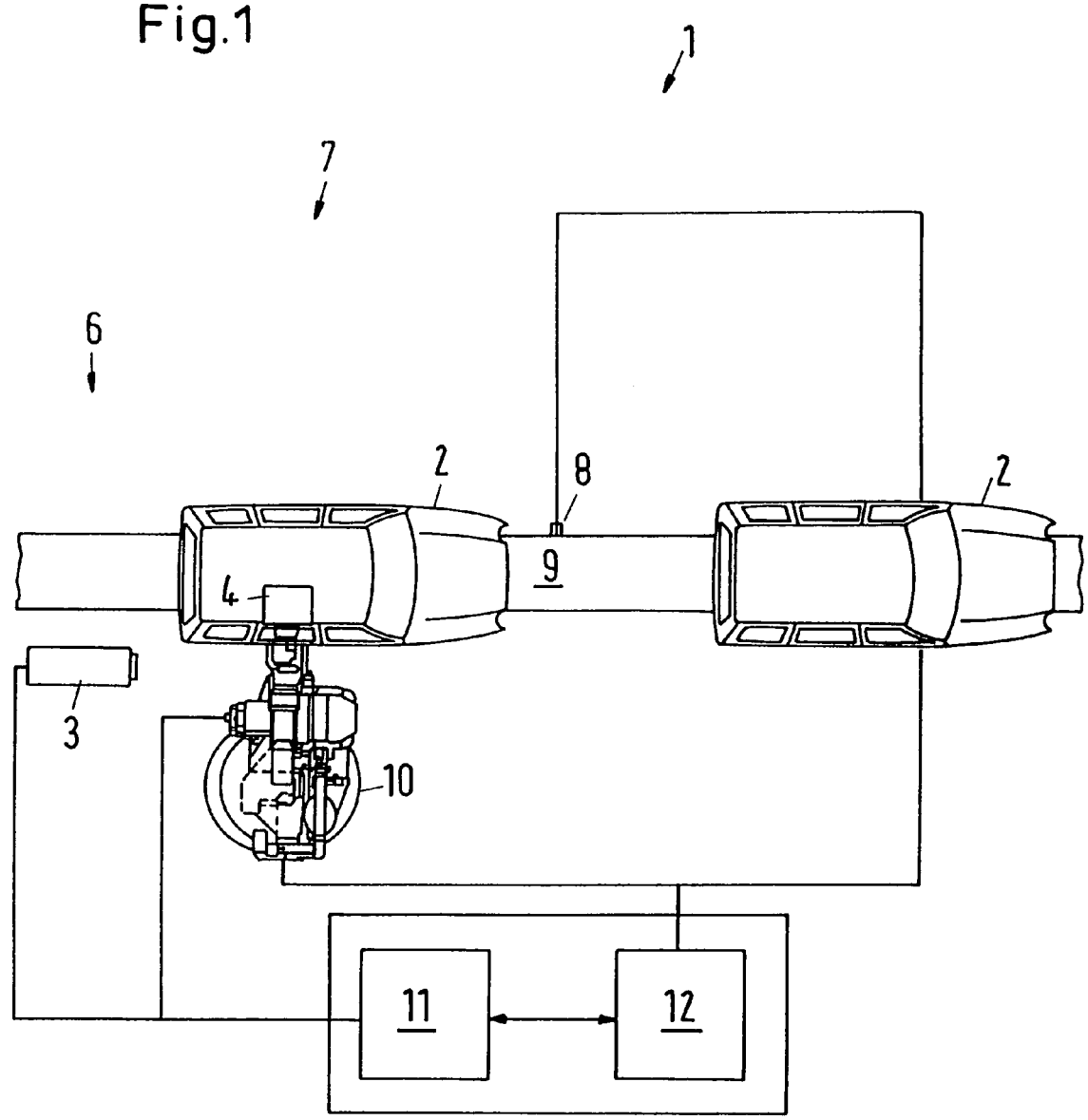
FIG. 1 is a schematic illustration of an inventive system for inspecting surfaces of a three-dimensional body, in a top view.

System 1 shown in FIG. 1 for inspecting surfaces of a three-dimensional body 2 is designed to examine a painted surface of bodies. The system is not limited to this application, however. Instead, it can be used in general to inspect any types of surfaces.

The system includes several cameras and illumination devices, which are subdivided into several inspection units 3 and 4 located at separate points. Stationary inspection unit 3 is a first subsystem 6 for examining the sides of body 2, and inspection unit 4 is a second subsystem 7 for examining the rest of the surface areas. It is also possible to provide further subsystems and to adapt the size of the inspection units to the particular circumstances. Subsystems 6, 7 are located one behind the other along a displacement device 9—designed as a conveyor belt—for body 2, so that body 2 is moved relative to stationary inspection unit 3 and, e.g., small-surface area or large-surface area inspection unit 4. In addition, inspection unit 4 is mounted on a displacement device 10 assigned to inspection unit 4, which allows inspection unit 4 to attain any possible orientation in space. Displacement device 10 is designed as a manipulator or handling device that allows inspection unit 4 to be moved in several degrees of freedom around various axes of rotation.

By way of body 2 moved on conveyor belt 9 and via displacement device 10 with inspection unit 4, a relative motion between the camera and the illumination device of inspection units 3, 4 and body 2 is produced, whereby pictures are taken of the areas to be inspected on the surface of three-dimensional body 2 at various points in time using the cameras of inspection units 3, 4. The pictures that are taken are analyzed in evaluation device 11 with the aid of image-evaluation algorithms.

To coordinate the relative motion between three-dimensional object 2 and the cameras and illumination devices of inspection units 3, 4, a control device 12 is provided that is set up such that the camera, the illumination device and the surface are brought into a defined geometric relationship with each other during the inspection of each area to be inspected on the surface of body 2, at least for the period of time required to take a picture. To this end, control device 12 knows, e.g., by performing a measurement with a sensor 8, the positions of body 2 moving on conveyor belt 9, and inspection units 3, 4. Inspection unit 4 mounted on displacement device 10 can also be brought into a specified position by control device 12 relative to the position of body 2, in which the defined geometric relationship between the surface of body 2 and the camera and illumination device of inspection unit 4 is attained. When this relationship is attained, a picture is taken of the area to be inspected, and the picture is evaluated by evaluation device 11.

Evaluation device 11 and control device 12 can be realized as separate computers or combined into one computer system.

Figure 2:
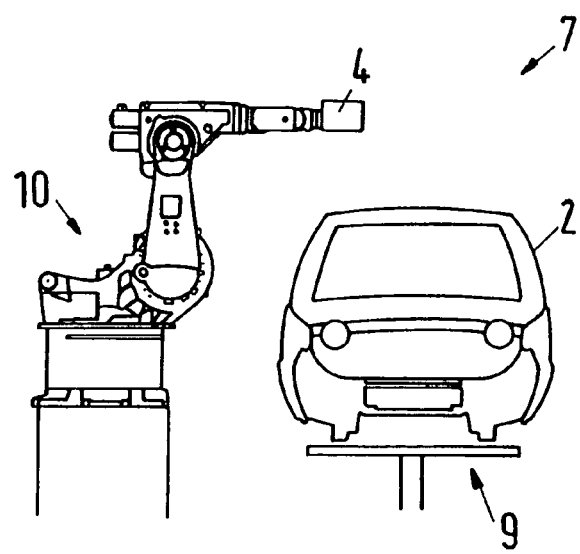
FIG. 2 shows part of the system in FIG. 1, in a side view.

FIG. 2 shows—in a side view from the front—an inspection unit 4 in second subsystem 7 of entire system 1 for inspecting surfaces mounted on a displacement device 10, in particular a manipulator or handling device. Inspection unit 4 can be positioned freely in space around various axes of rotation of displacement device 10, so that a specified distance and a specified angular relationship to the surface normal of the area to be inspected can be adjusted for a certain surface area on body 2. The defined geometric relationship is then attained.

Basically, the examination of the surface can also be carried out using only one inspection unit that is freely movable in space. The subdivision into several subsystems 6, 7 located on a conveyor belt 9 of body 2 to be inspected makes time-optimized work possible, however, since inspection units 3, 4 can operate at least partially simultaneously in order to simultaneously scan various areas to be inspected on body 2. The relative motion between body 2 and inspection units 3, 4 is coordinated by control device 12, so that moving object 2 and all displacement devices 9, 10 are synchronized. Subsystems 6, 7 are not limited to two, and each subsystem 6, 7 can have several different inspection units.

Instead of inspection units 3, 4, in which both a camera and an illumination device are located, it is also possible to locate individual illumination devices and individual cameras in a mobile or stationary manner around movable body such that the camera, illumination device and the surface are in a defined geometric relationship with each other during the inspection of each area to be inspected on the surface, for the period of time required to take at least one picture. In this case, the task of control device 12 is simplified, but the flexibility of system 1 decreases.

An inspection unit 3, 4 is composed, e.g., of parallel tubes for illumination, with cameras provided between them, with which the area illuminated by the tubes can be monitored in bright and dark fields. All other combinations of suitable picture-taking devices—in the form of cameras—and suitable illumination devices are also possible.

The method for inspecting surfaces of three-dimensional body 2 is described again in detail below.

Figure 3:
FIG. 3 shows typical structures of surface flaws.

While three-dimensional body 2 moves on conveyor belt 9, various areas to be inspected are covered by the cameras and illumination devices of inspection units 3, 4. Inspection unit 4 can also be brought into a desired position. Control unit 12 recognizes the position of body 2 and each of the inspections units 3, 4 in space. Based on these known positions, control device 12 determines whether the specified geometric relationship between the camera, the illumination device and the area to be inspected on the surface has been attained. In this case, control device 12 issues a control command to take a picture, and the picture is then analyzed in evaluation unit 11 with the aid of image-evaluation algorithms. The following can be taken into account: The contrast, size, the relationship between size and contrast, the geometry and contour, and the arrangement in the bright and dark field when bright/dark field illumination is used. As a result, it is possible to detect main topological surface defects 13 in the paint surface on body 2. Topological defects 13 of this type are positive and/or negative deformations on the target surface, as shown in FIG. 3 as an example. Surface defects 13 can be caused by soiling, craters, solvent boils, pin-holes, wet impressions, scratches or the like, or by wetting problems in the painting process.

The data detected in the image evaluation are used to classify defects 13. Based on the classification of the various defects, it can be determined, among other things, whether it is a relevant defect 13 or whether these defects 13 can be disregarded. For instance, surfaces that are slightly uneven—similar to the surface of an orange peel—can usually be disregarded. A minimum deviation in the surface normal in the area of the defect from the surroundings around the defect can serve as the criterium therefor. The classification can be designed to be adjustable, parameterizable and/or self-learning, in particular. In addition, the classification can also distinguish between various defects and defect types. The classification is therefore not limited to differentiation between defects and non-defects.

With the inventive method and corresponding system 1, which is used, in particular, to carry out the method for inspecting surfaces of a three-dimensional body, it is possible, due to the unambiguously specified, defined geometric relationship between the surface of body 2 and the camera and the illumination device assigned to this camera, to always create optimum conditions for detecting a defect on the surface.

REFERENCE NUMERALS

1 System
2 Three-dimensional body, body
3 Inspection unit
4 Inspection unit
6 First subsystem
7 Second subsystem
8 Sensor
9 Displacement device, conveyor belt
10 Displacement device, manipulator or handling device
11 Evaluation device, computer
12 Control device, computer
13 Surface defect

What is claimed is:

1. A method for inspecting a surface of a three-dimensional body, said method comprising the steps of:
   a) moving at least one camera and at least one illuminating device relative to the surface of the three-dimensional body;
   b) taking pictures of areas to be inspected on the surface during movement of the at least one camera relative to the surface of the three-dimensional body in step a); and
   c) transmitting the pictures taken by the at least one camera in step b) to a computer and evaluating the pictures in the computer;
   wherein the at least one camera, the at least one illumination device and the surface are brought into several respective different defined geometric relationships with each other during inspection of each of the areas to be inspected on the surface, at least for a time period required to take one of the pictures.

2. The method as defined in claim 1, wherein the several respective different defined geometric relationships are determined by corresponding angles between surface normals of the areas to be inspected and the at least one illumination device or the at least one camera or by corresponding distances between the areas to be inspected and the at least one illumination device or the at least one camera.

3. The method as defined in claim 1, wherein said areas to be inspected are selected to be different-sized according to curvatures of the surface on which the areas to be inspected are located.

4. The method as defined in claim 1, wherein at least one of the at least one camera, the at least one illumination device and the three-dimensional body is movable in one or more degrees of freedom.

5. The method as defined in claim 1, wherein the at least one illumination device illuminates the surface to be inspected in a diffuse, directed or structured manner with sustained illumination and/or flash illumination.

6. The method as defined in claim 1, wherein the at least one illumination device illuminates the surface to be inspected with at least one of an alternating dark field illumination, an alternating bright field illumination and a two-dimensional illumination.

7. The method as defined in claim 1, wherein several of said pictures are taken of each of the areas on the surface to be inspected using various illumination situations and/or different camera settings.

8. The method as defined in claim 1, wherein several cameras and several illumination devices are combined to form at least two subsystems that are movable relative to the surface to be inspected, said subsystems being interconnected via a communication interface, and an inspection result being created by the evaluating of the pictures from several or all of said subsystems.

9. The method as defined in claim 1, wherein the evaluating of the pictures that were taken by the at least one camera employs image-evaluation algorithms stored in a computer system.

10. The method as defined in claim 9, wherein during the evaluating of the pictures predetermined structures detected in the pictures are not identified as defects.

11. The method as defined in claim 1, wherein relative positions between the areas on the surface to be inspected and the at least one camera and/or the at least one illumination device are detected, and said pictures are taken with a controlled resolution, position and/or time according to the relative positions.

12. The method as defined in claim 1, wherein specified areas to be inspected on the surface are examined with different settings of the respective different defined geometric relationships, of illumination from the at least one illumination device and/or of image-processing parameters.

13. A system for inspecting a surface of a three-dimensional body, said system comprising
   at least one camera for taking pictures of areas to be inspected on the surface;
   at least one illumination device for illuminating the areas to be inspected;
   at least one displacement device that moves the at least one camera and/or the at least one illumination device relative to the three-dimensional body, wherein the at least one camera takes the pictures of the object to be inspected during movement of the at least one camera relative to the three-dimensional body;

an evaluation unit for evaluating the pictures taken by the at least one camera; and a control device for bringing the at least one camera, the at least one illumination device and the surface to be inspected into plural respective different defined geometric relationships with each other during the inspecting of each of the areas to be inspected on the surface, at least for a time period required to take one of the pictures.

14. The system as defined in claim 13, including a single inspection unit in which said at least one camera and said at least one illumination device are located.

15. The system as defined in claim 13, including several cameras, several illumination devices and separate inspection units, and wherein the separate inspective units each include at least one of the several cameras and at least one of the several illumination devices and represent separate subsystems.

16. The system as defined in claim 15, wherein said separate subsystems include at least one stationary subsystem and at least one movable subsystem.

17. The system as defined in claim 13, wherein said at least one camera is calibrated three-dimensionally.

18. The system as defined in claim 13, wherein said at least one camera is calibrated with reference to the at least one illumination device, the three-dimensional body and/or the at least one displacement device.

* * * * *